US00PP21179P3

(12) United States Plant Patent

McGranahan et al.

(10) Patent No.: US PP21,179 P3

(45) Date of Patent: Aug. 3, 2010

(54) WALNUT ROOTSTOCK 'VX211'

(50) Latin Name: *Juglans hindsii×Juglans regia*
Varietal Denomination: VX211

(75) Inventors: Gale McGranahan, Davis, CA (US); Charles Leslie, Davis, CA (US); Wesley Hackett, Davis, CA (US); Gregory Browne, Davis, CA (US); James McKenna, West Lafayette, IN (US); Thomas Buzo, Reedley, CA (US); Stephanie Kaku, Fresno, CA (US); Michael McKenry, Selma, CA (US)

(73) Assignees: The Regents of the University of California, Oakland, CA (US); The United States of America, as represented by the Secretary of Agriculture, Washington, DC (US)

( * ) Notice: Subject to any disclaimer, the term of this patent is extended or adjusted under 35 U.S.C. 154(b) by 214 days.

(21) Appl. No.: 11/821,844

(22) Filed: Jun. 25, 2007

(65) Prior Publication Data

US 2008/0320618 P1 Dec. 25, 2008

(51) Int. Cl.
*A01H 5/00* (2006.01)

(52) U.S. Cl. ..... Plt./154

(58) Field of Classification Search ..... Plt./154
See application file for complete search history.

(56) References Cited

OTHER PUBLICATIONS

McGranahan, Gale. Nurseries Licensed to Sell New Clonal Walnut Rootstocks. Walnut Improvement Program, UC Davis. May 1, 2008. Available at: http://cesutter.ucdavis.edu/files/51594.pdf.*

McGranahan, G. et al. (1996). "The Paradox Diversity Study," Walnut Research Reports 1996, pp. 43-48.

Browne, G.T. et al. (1998). "Strategies for Control of Phytophthora Root and Crown Rots of Walnut," Walnut Research Reports 1997, pp. 381-391.

McGranahan, G. et al. (1998). "The Paradox Diversity Study," Walnut Research Reports 1997, pp. 55-63.

Browne, G.T. et al. (1999). "Strategies For Control of Phytophthora Root and Crown Rots of Walnut," Walnut Research Reports 1998, pp. 361-371.

McKenna, J. et al. (1999). "The Paradox Genetic Diversity Study," Walnut Research Reports 1998, pp. 40-65.

Browne, G. (2001). "Strategies for Management of Phytophthora on Walnut: Evaluating Potential of Elite Paradox Clones and Wingnut Families," Walnut Research Reports 2000, pp. 429-436.

McKenry, M. et al. (2001). "A Three-Year Search for Nematode Resistance in Walnut-Final Report," Walnut Research Reports 2000, pp. 509-512.

Browne, G. (2002). "Strategies for Management of Phytophthora on Walnut: Evaluating Potential of Elite Paradox Clones and Wingnut Families," Walnut Research Reports 2001, pp. 101-109.

Hackett, W.P. et al. (2003). "Propagation and Retesting of Walnut Rootstock Genotypes Putatively Resistant to Pests and Diseases," Walnut Research Reports 2002, pp. 99-107.

Browne, G.T. et al. (2004). "Evaluation of Resistance to Phytophthora citricola Among Diverse Clones of Paradox Hybrid Rootstocks," Proceedings of the Vth International Walnut Symposium, Sorrento, Italy, pp. 395-405.

Hackett, W.P. et al. (2004). "Propagation and Retesting of Walnut Rootstock Genotypes Putatively Resistant to Pests and Diseases," Walnut Research Reports 2003,pp. 85-95.

McKenry, M. (2004). "Field Evaluations/Inputs for Grower Replant Settings and New Lines of Nematode Resistance," Walnut Research Reports 2003, pp. 431-439.

Browne, G. et al. (2005). "Determining Phytophthora Resistance in Elite Paradox Clones and Specific Etiology of a Paradox Crown and Root Rot," Walnut Research Reports 2004, pp. 379-387.

Hackett, W.P. et al. (2005). "Propagation and Retesting of Walnut Rootstock Genotypes Putatively Resistant to Pests and Diseases," Walnut Research Reports 2004, pp. 89-95.

McKenry, M. (2005). "Field Evaluations/Inputs for Grower Replant Settings and New Lines of Nematode Resistance," Walnut Research Reports 2004, pp. 407-415.

McKenry, M. (2006). "Field Evaluations/Inputs for Grower Replant Settings and New Lines of Nematode Resistance," Walnut Research Reports 2005, pp. 365-371.

McGranahan, G. et al. (2006). "Clonal Propagation of Walnut Rootstock Genotypes for Genetic Improvement," Walnut Research Reports 2005, pp. 85-93.

Browne, G. et al. (2006). "Biology and Management of Phytophthora Crown and Root Rot of Walnut," Walnut Research Reports 2005, pp. 335-344.

McKenry, M. (2007). "Filed Evaluations/Inputs for Grower Replant Settings and New Lines of Nematode Resistance," Walnut Research Reports 2006, pp. 279-283.

Grant, J. et al. (2007). "Orchard Performance of Selected Clonal Paradox Rootstocks," Walnut Research Reports 2006, pp. 79-81.

McGranahan, G. et al. (2007). "Clonal Propagation of Walnut Rootstock Genotypes for Genetic Improvement 2006," Walnut Research Reports 2006, pp. 71-78.

Browne, G. T. et al. (1999-2000). Project Plan/Research Grant Proposal for Year 4 of 5 of "Strategies for Control of Phytophthora Root and Crown Rots of Walnut," University of California Division of Agricultural Sciences, 6 pages.

Browne, G. T. et al. (2004-2005). Project Plan/Research Grant Proposal for Year 1 of 2 of "Determining Phytophthora Resistance in Elite Paradox Clones and Specific Etiology of a Paradox Crown and Root Rot," University of California Division of Agricultural Sciences, 5 pages.

* cited by examiner

*Primary Examiner*—Wendy C Haas
(74) *Attorney, Agent, or Firm*—Morrison & Foerster LLP

(57) ABSTRACT

A new and distinct variety of walnut rootstock denominated 'VX211' is described. This new variety, 'VX211', can be propagated through standard tissue culture micropropagation or rooted cuttings. 'VX211' has vigor and survivability in the nursery and in the orchard. It has reduced susceptibility to damage from nematodes (*Pratylenchus vulnus*) compared to other 'Paradox' rootstock. 'VX211' also has reduced susceptibility to damage from *Phytophthora citricola* in greenhouse screens and in the field compared to other 'Paradox' rootstock.

10 Drawing Sheets

Latin name: Botanical/commercial classification: (*Juglans hindsii×Juglans regia*)/new 'Paradox' walnut rootstock.

Varietal denomination: The varietal denomination of the claimed walnut rootstock is 'VX211'.

BACKGROUND OF INVENTION

The present invention relates to a new and distinct clonal rootstock of 'Paradox' (not patented) walnut tree (*Juglans hindsii*×*Juglans regia*) that has been denominated varietally as 'VX211', and more particularly to such a walnut rootstock that is vigorous, that has reduced susceptibility to nematodes (*Pratylenchus vulnus*) and *Phytophthora* (*Phytophthora citricola*), and that further is easily clonally propagated by standard tissue culture micropropagation.

It has long been recognized as desirable to provide vigorous walnut rootstocks that have increased resistance to soil pests and diseases, specifically nematodes (*Pratylenchus vulnus*) and *Phytophthora* (*Phytophthora citricola*). The rootstock of the present variety, 'VX211', is similar to other 'Paradox' walnut rootstocks (*Juglans hindsii*×*Juglans regia*), except that it has increased resistance or tolerance to *Pratylenchus vulnus* and *Phytophthora citricola* and can be easily micropropagated to produce a vigorous clonal 'Paradox' rootstock.

SUMMARY OF THE INVENTION

It was found that the walnut rootstock 'VX211' of the present invention exhibits the following combination of characteristics:

a) can be propagated through standard tissue culture micropropagation or rooted cuttings;
b) has vigor and survivability in the nursery and in the orchard;
c) has reduced susceptibility to damage from nematodes (*Pratylenchus vulnus*) compared to other 'Paradox' rootstock; an
d) has reduced susceptibility to damage from *Phytophthora citricola* in greenhouse screens and in the field compared to other 'Paradox' rootstock.

BRIEF DESCRIPTION OF THE TABLES

Table 1 shows comparative nursery performance of 'VX211' and other walnut rootstock clones.

Table 2 shows growth rating and diameters for 'VX211' and other rootstock clones.

Table 3 shows field performance of clonal 'Paradox' walnut hybrids, Northern California black walnut and Chinese wingnut rootstocks in non-infested soil and soil infested with *Phytophthora.*

DETAILED DESCRIPTION OF THE INVENTION

Figure 1:
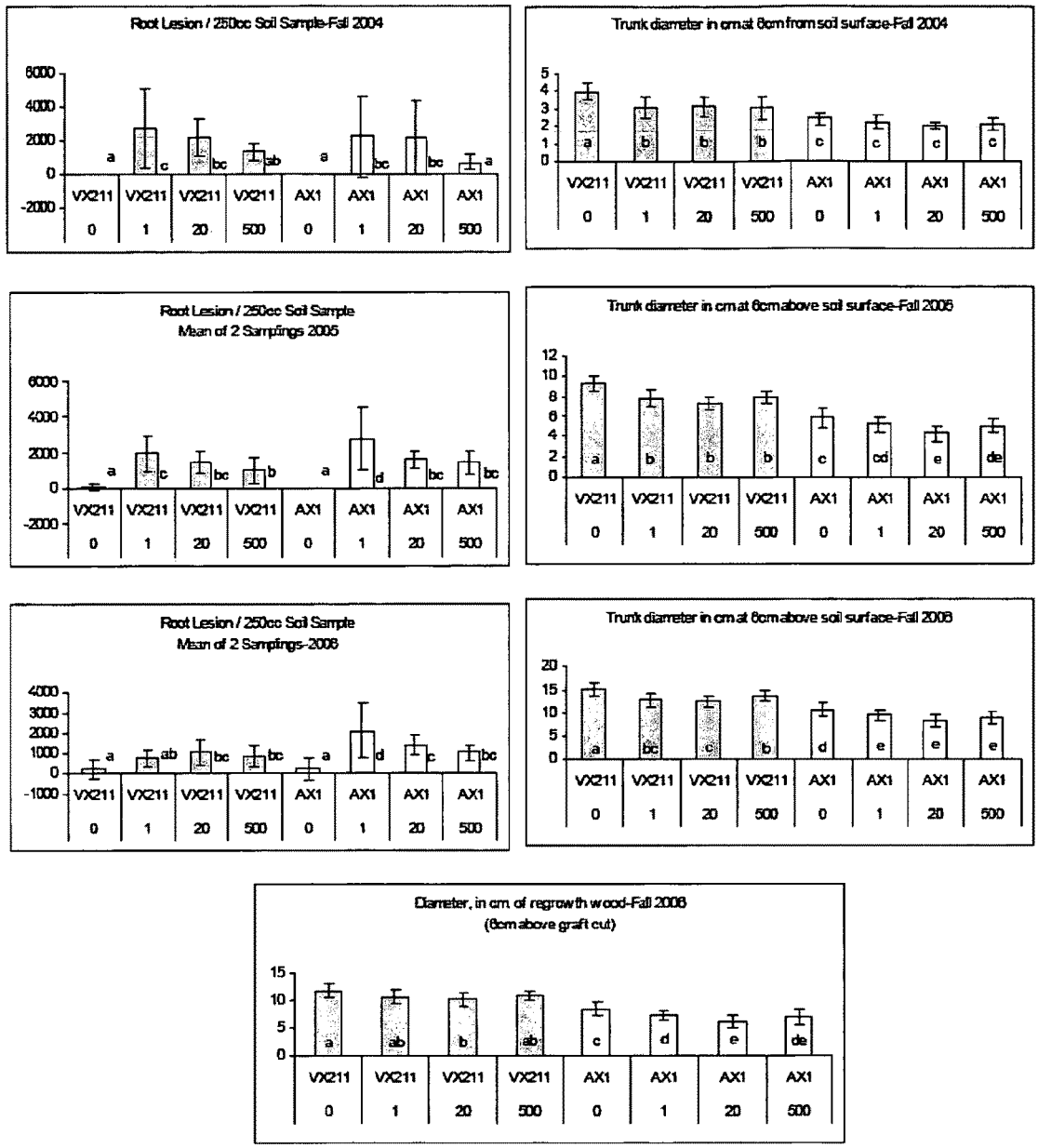
FIG. 1 shows performance of 'VX211' compared to 'AX1' under pressure from nematodes at varying densities.

The new rootstock of the present invention was selected as part of the "Paradox Diversity Study" (PDS) which was initiated in 1996 to study the genetic diversity of commercial 'Paradox' sources. The study included approximately 300–500 seeds each (depending on the predicted percent 'Paradox'), from 37 black walnut sources of 'Paradox' provided by California walnut nurseries, and seven controlled crosses made in Davis, Calif. and open-pollinated controls from different *Juglans* species. Seeds were germinated and grown at 3 different nurseries for one year and then seedlings were distributed to cooperating researchers for tests of response to nematodes, *Phytophthora* (seed supplied), crown gall (*Agrobacterium tumefaciens*) and the field environment (field trials). The study was repeated in 1997.

The rootstock of the present invention was evaluated for response to nematodes in 1998 along with 9 siblings and the remaining rootstock families. One-year old seedlings were planted on 1.2 or 1.8 meter spacing with 3.35 meter centers. The field test site was infested with a single population of root lesion nematode (*P. vulnus*) originally placed on site in 1976. At planting time seedlings were inoculated with additional *P. vulnus*. Each fall 20 grams of root tissue were collected from each tree. These roots were placed in a mist chamber for 5 days for nematode extraction and nematodes/gram root was calculated.

In July 1998 it was evident that one seedling ('VX211') was more vigorous than the others, but in the fall the nematodes were abundant on the roots of 'VX211'. In July 1999 roots were collected and again nematodes were found to be abundant, but the seedling 'VX211' continued to be more vigorous than the other seedlings in spite of the nematodes. Due to its apparent superiority it was transplanted to a "mother block" at an agriculture center in Parlier, Calif. In winter 2000–2001 propagating wood was collected. 'VX211' was propagated by hardwood cuttings. Additionally, 'VX211' was asexually reproduced by standard tissue culture micropropagation in Davis, Calif. In 2002 a "stock block" was established in Davis, Calif. with 6 trees of 'VX211' as well as other promising selections.

Propagation of 'VX211' both by standard hardwood cuttings and by standard tissue culture micropropagation was successful. From November 2002 to October 2003, 212 'VX211' plants were micropropagated, rooted in gelled medium and acclimatized in the greenhouse; 153 (72%) survived. When rooted ex vitro, 126/184 (68%) survived. Hardwood cuttings rooted between 73% (11/15) to 87% (13/15). By November 2003 there were 187 available for field trials and 60 available for *Phytophthora* screening.

In March 2004, 48 plants of the 'VX211' clone and a standard 'Paradox' ('AX1') were evaluated for additional nematode screening and comparison. These were planted in $1/100^{th}$ acre macroplots. The macroplots had concrete sides 1.5 meter deep into the soil with open bottoms and were nematode-free. 'VX211' and 'AX1' were planted side by side in 48 separate macroplots infested with 0, 1, 20, or 500 *P. vulnus* nematodes per 250 cc of soil. Tree diameters and number of nematodes on the roots were determined 2004–2006 (FIG. 1). Nematodes built up quickly but 'VX211' was 30% taller in the first year and the diameter of 'VX211' was significantly greater than 'AX1' in all three years (FIG. 1). The vigor of 'VX211' under pressure from nematodes suggests that 'VX211' has a means to avoid or escape severe damage from nematodes.

In spring 2004, 106 plants of 'VX211' produced through standard tissue culture micropropagation were planted in a nursery along with over 1800 plants of 17 different clones. At the end of the growing season 'VX211' was the most vigorous of all clones (Table 1) demonstrating that propagation is true-to-type through successive generations. Eighty-two percent were graftable and the mean diameter was 31 mm at 5 cm from the soil surface.

Graftable trees were distributed for grafted field trials in 5 different orchards in replant situations in 2005. Grafting posed no problem and 'VX211' is considered compatible with English walnut scions. It is a typical 'Paradox' in that respect. In addition, 30 each of 11 different genoptypes including 'VX211' were planted in May 2005 in Davis, Calif. for artificial inoculation with *Phytophthora citricola*. A randomized block split plot design was used. For each rootstock clone, there were six four-tree plots to be infested and six single-tree plots to serve as non-infested controls. Northern California black (*Juglans hindsii*) and wingnut (*Pterocarya stenoptera*) were included as susceptible and resistant controls, respectively. In January 2006, 100 ml of a V8 juice-oat mixture infested with *Phytophthora citricola* was mixed into the upper 5 cm of soil around the trunk of each tree. A sterile mixture was applied to the uninoculated controls.

Figure 2:
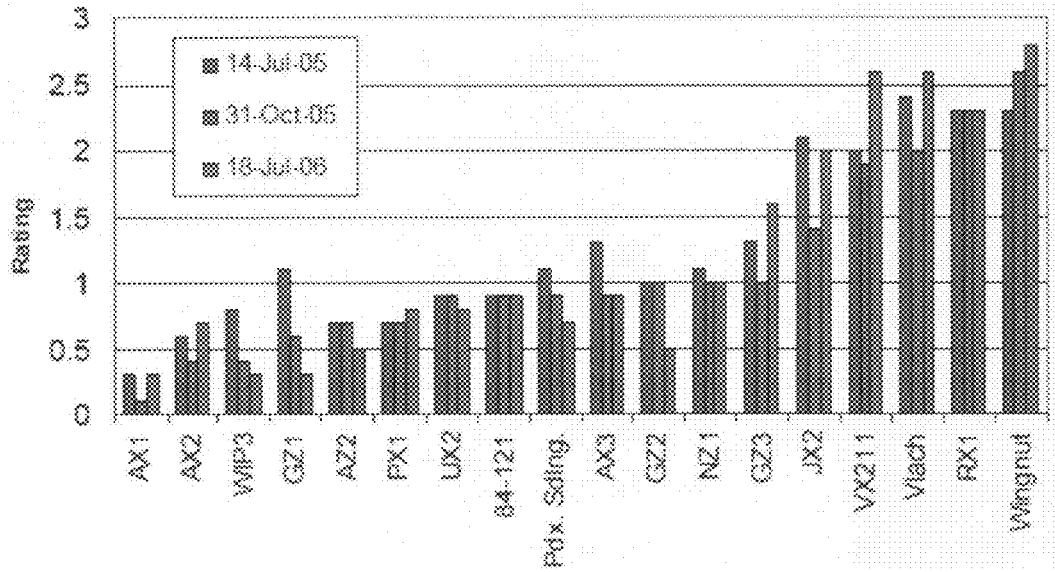
FIG. 2 shows a visual rating of tree growth and condition of clonal and seedling test trees at a Jenny Lind, Calif. field site.
Figure 3:
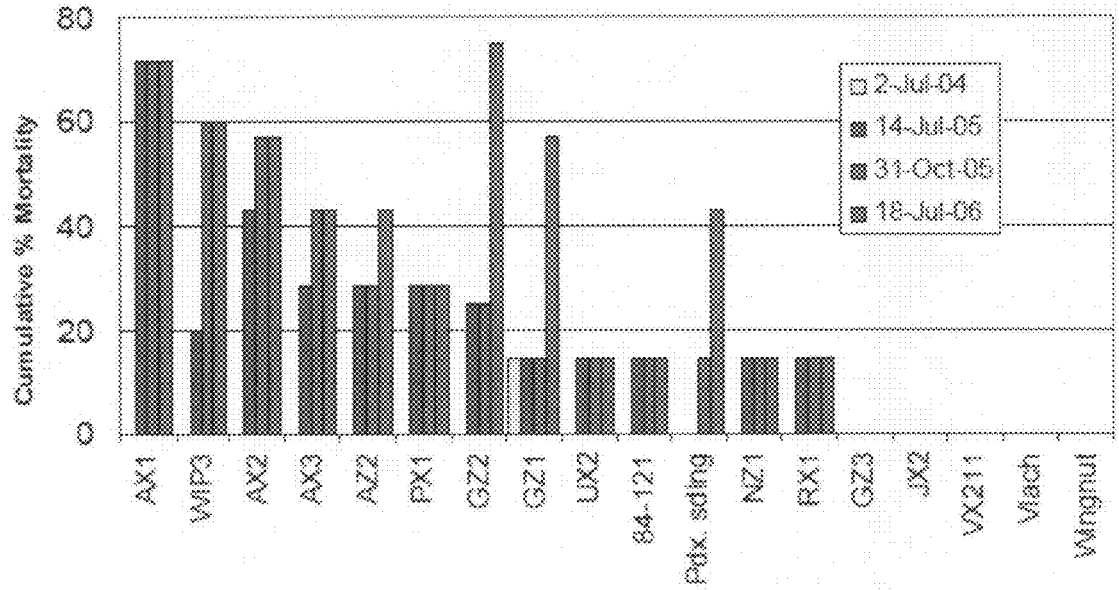
FIG. 3 shows cumulative percent mortality of clonal and seedling test trees at a Jenny Lind, Calif. field site.
Figure 4:
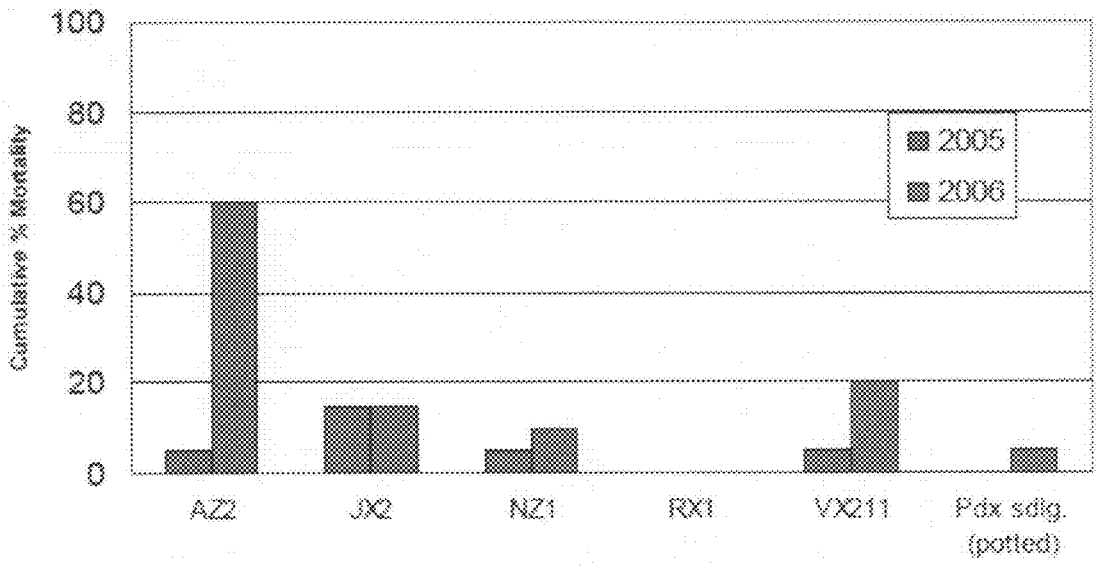
FIG. 4 shows tree mortality of clonal and seedling test trees at a Linden, Calif. field site.

Early results from several of the grafted field trials are shown (FIGS. 2–4; Table 2). In all cases 'VX211' was one of the superior clones. The block artificially inoculated with *Phytophthora* was assessed for growth in trunk circumference and development of crown rot as indicated by trunk cankers extending up from the soil surface in November 2006. Sixty-two percent of the susceptible controls were rotted or dead. The uninoculated controls of 'VX211' were the most vigorous trees in the block apart from the wingnut controls. No cankers were found on 'VX211' or many of the other clones, however the *Phytophthora* inoculation did appear to depress growth somewhat in 'VX211' (Table 3).

Figure 5:
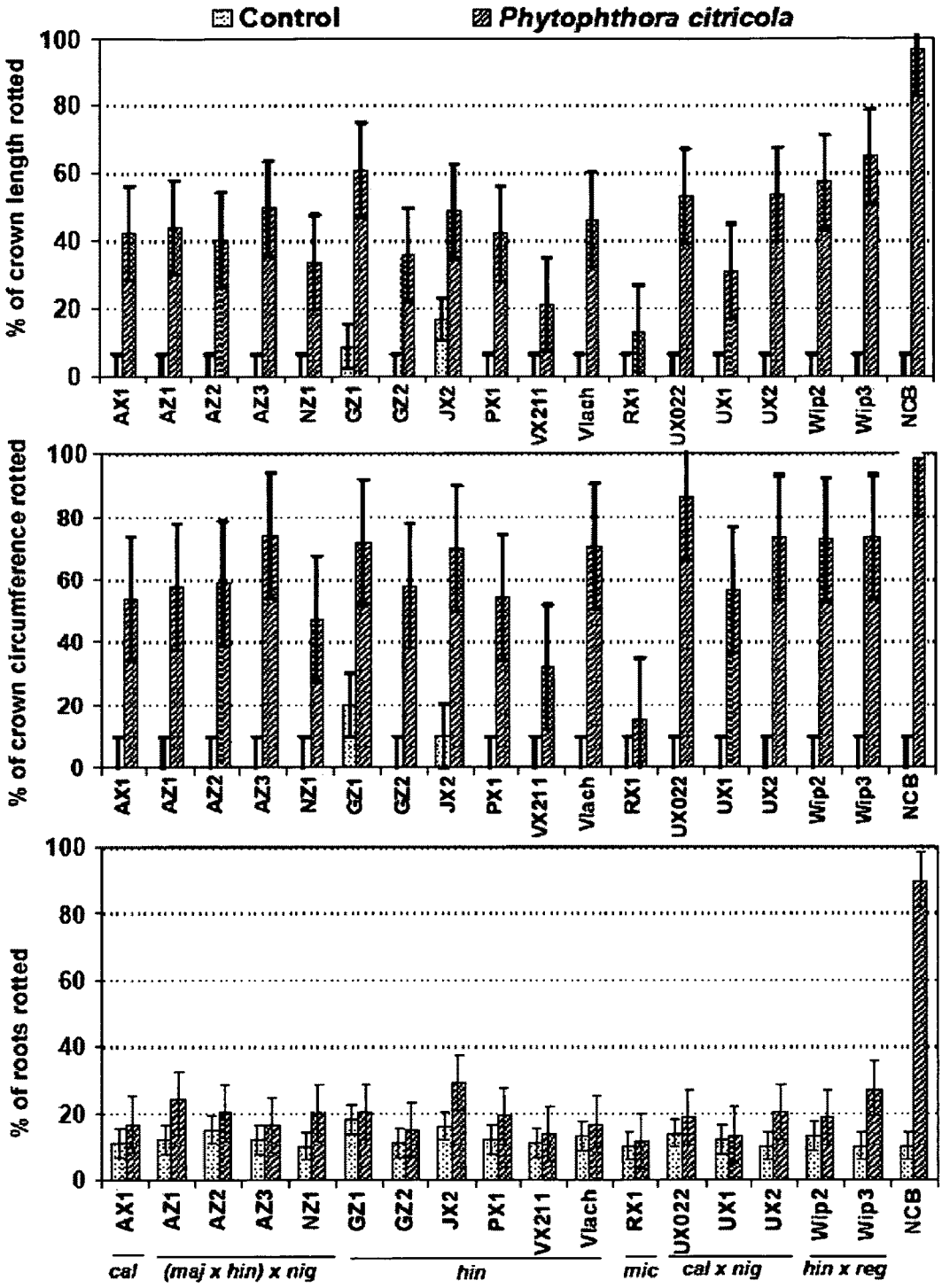
FIG. 5 shows relative resistance to *Phytophthora citricola* among clonal and seedling test trees in greenhouse experiment.

Simultaneously with field trials, greenhouse trials were carried out to assess the relative susceptibility of 'VX211' and other selected clones to *Phytophthora citricola*. Standard *Phytophthora* screening methods were used. Clonal selections including 'VX211' were micropropagated, rooted, acclimatized and chilled, and at 2–6 months were transplanted to pots of artificially inoculated soil. Four isolates of *P. citricola* from different districts of California were used to infest the soil. The isolates were grown in separate jars of V8 juice-oat-vermiculite substrate for one month, mixed in equal proportions and mixed in the soil (40 ml inoculated substrate per liter of soil). Starting two weeks after transplanting, all plants received 48-hour periods of soil flooding every two weeks. Three months after transplanting, soil was washed from the plants and the incidence and severity of crown rot were determined. One selected clone, 'VX211' consistently showed moderate resistance. The results from 2006 trials are shown in FIG. 5.

BOTANICAL DESCRIPTION OF THE PLANT

This description is based on the original selection of 'VX211', ungrafted, at ten years of age, a 3-year old ungrafted tree in *Phytophthora* field screen, and a greenhouse-grown plant at 6 months of age. Figures are also shown of a grafted 'VX211' tree. Data for the botanical description were collected in spring 2007.

The Munsell Color Charts for Plant Tissues (1977. Gretag-Macbeth, New Windsor N.Y.) is used in the identification of color. Also, common color terms are to be accorded their ordinary dictionary significance, Botanical classification: *Juglans hindsii*×*Juglans regia.*

Female parent: *Juglans hindsii.*

Male parent: *Juglans regia.*

'VX211' differs from its female parent by having fewer leaflets/leaf, broader leaflets and hybrid vigor. 'VX211' differs from its male parent by having more leaflets/leaf and hybrid vigor. 'VX211' does not differ substantially from other similar hybrids except in its superior performance under adverse soil conditions as described in the "Background of the Invention".

Figure 6:
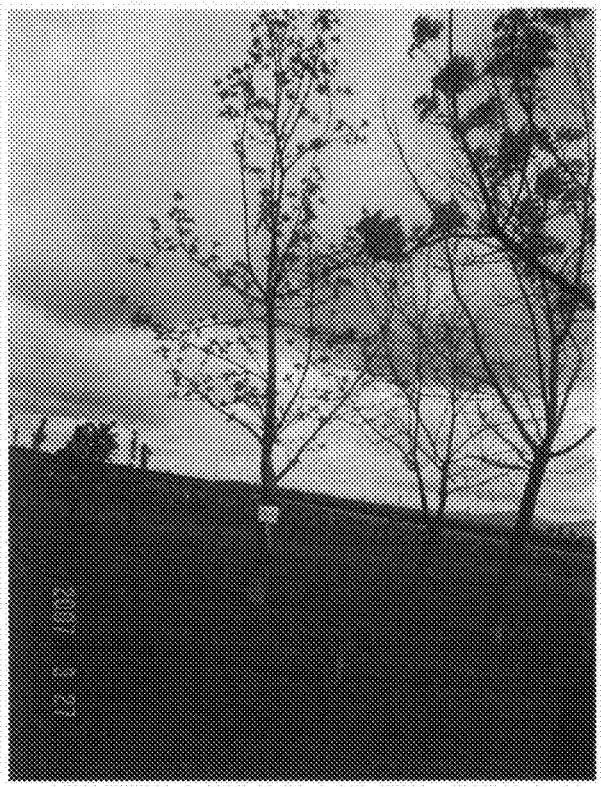
FIG. 6 shows 'VX211' at 10 years of age.
Figure 7:
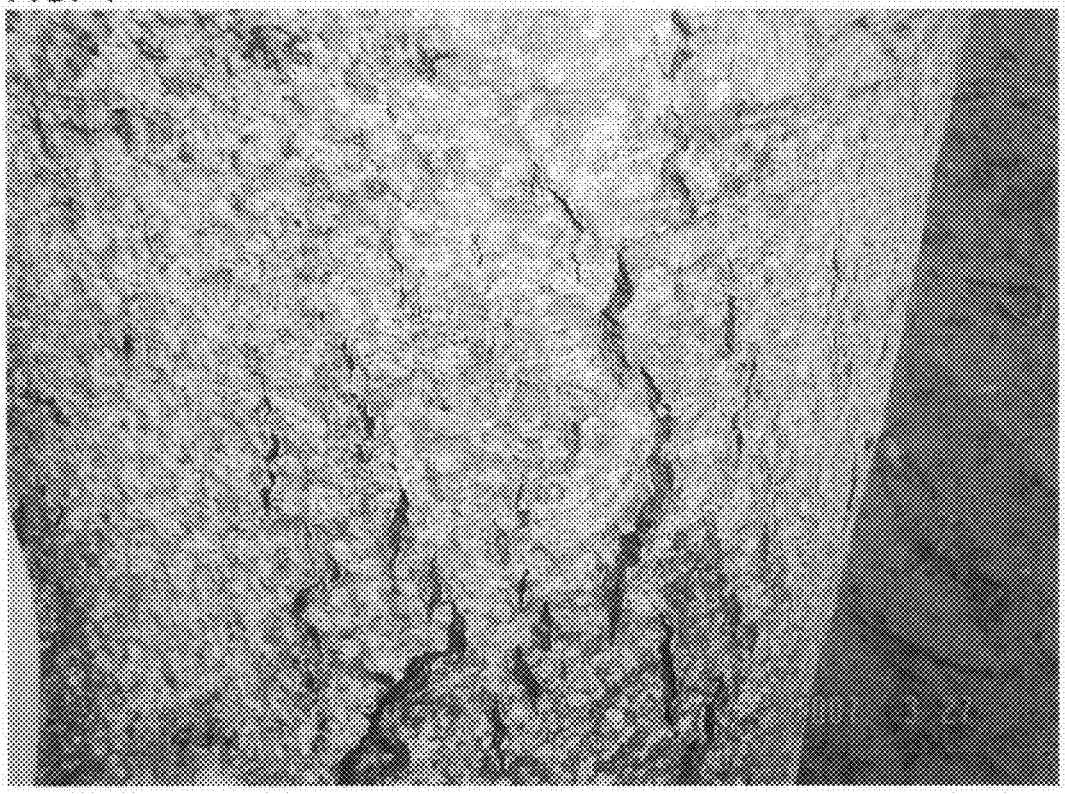
FIG. 7 shows bark of ten-year old 'VX211'.
Figure 8:
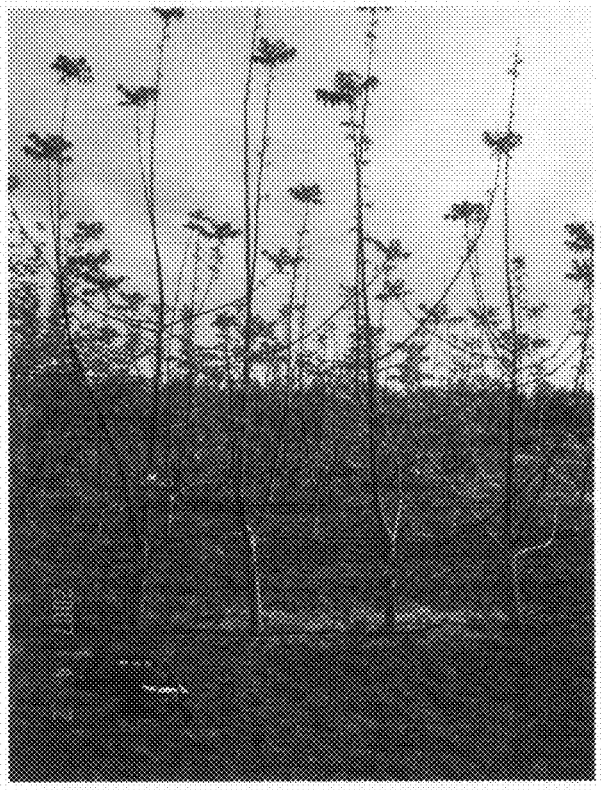
FIG. 8 shows several three-year old trees of 'VX211'.
Figure 9:
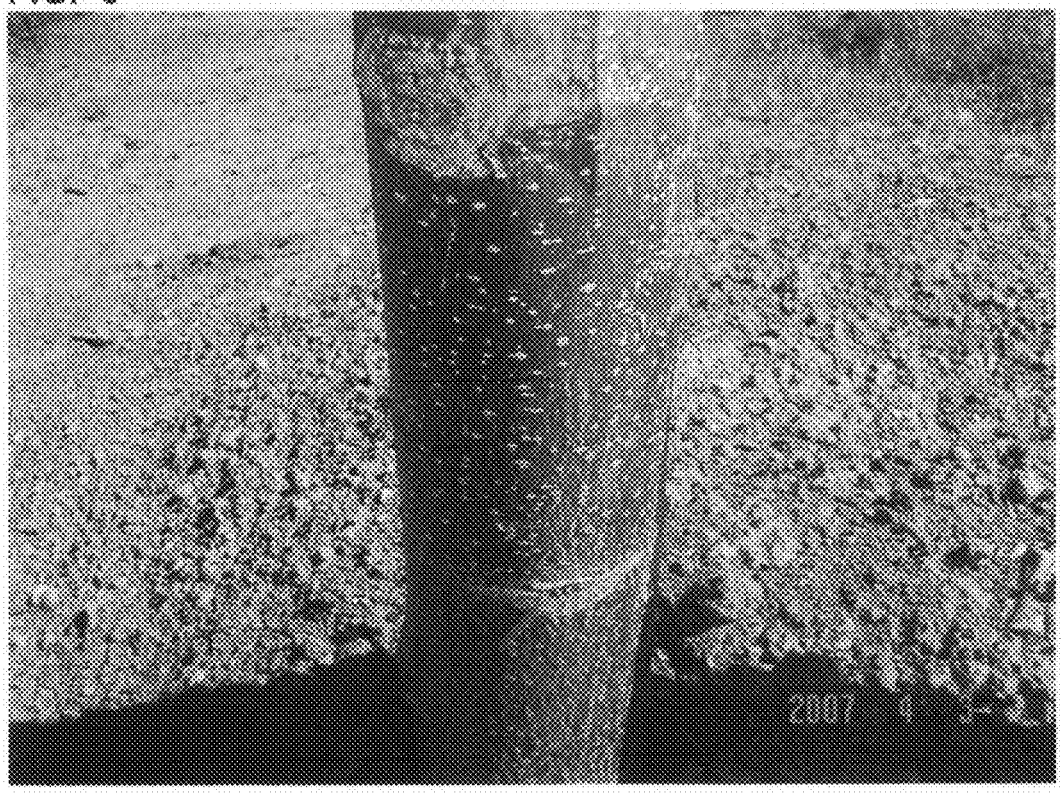
FIG. 9 shows bark at base of three-year old 'VX211'.
Figure 10:
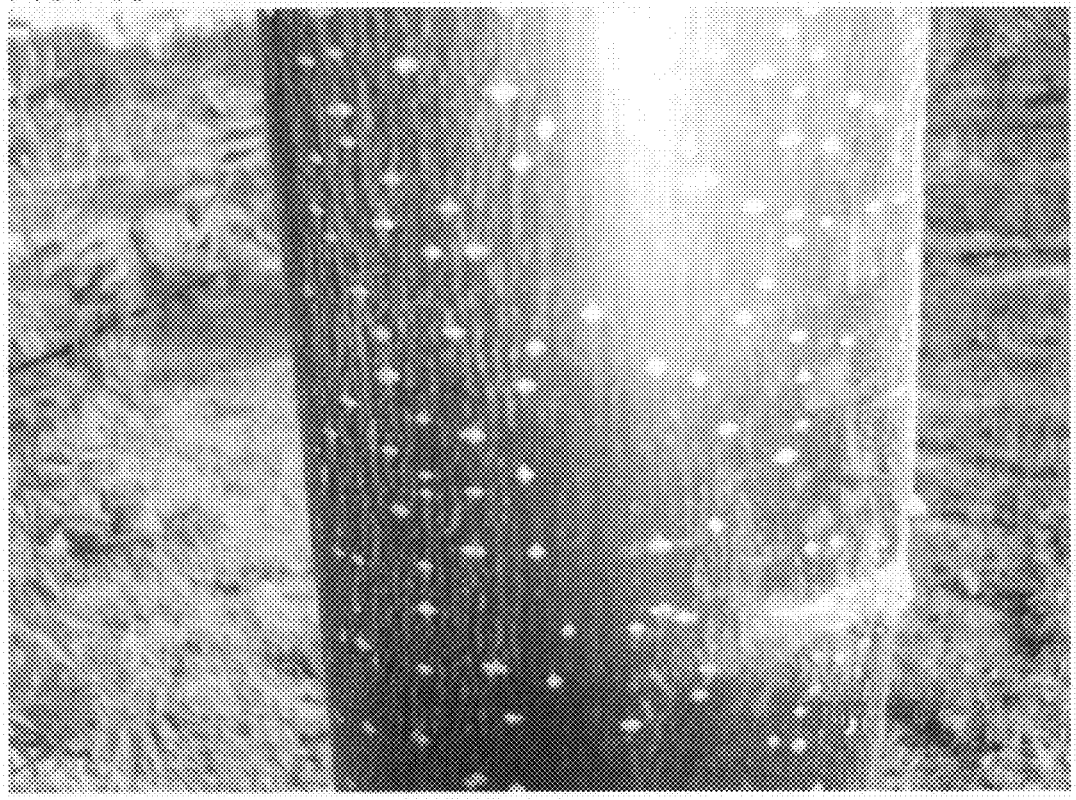
FIG. 10 shows bark and lenticels farther up the stem of 'VX211'.
Figure 11:
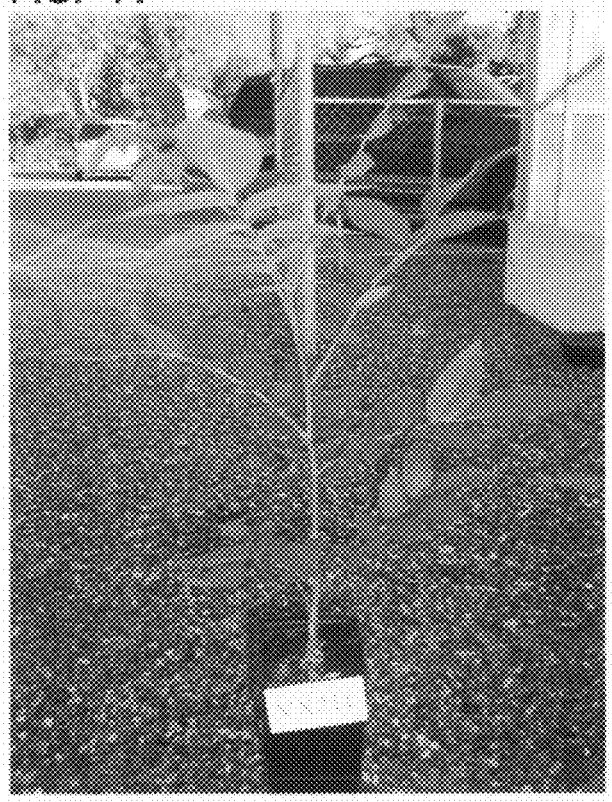
FIG. 11 shows 6-month old greenhouse grown 'VX211'.
Figure 12:
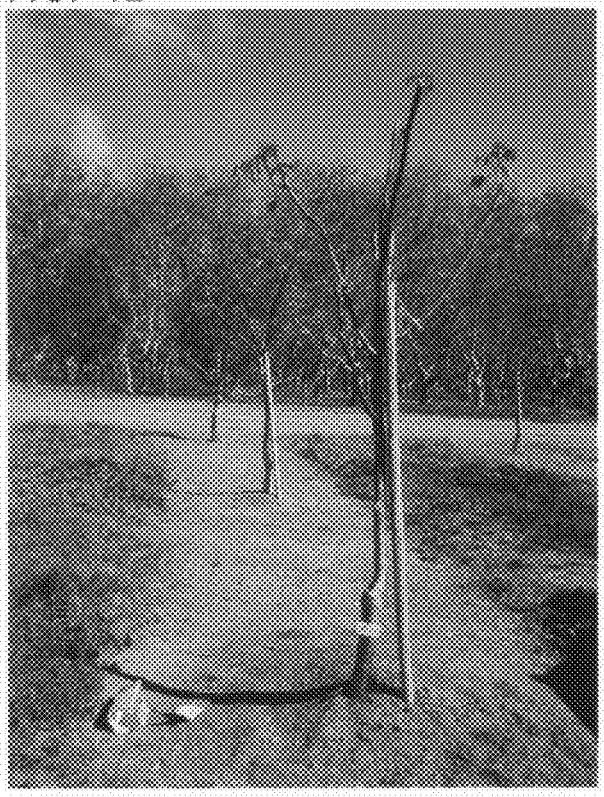
FIG. 12 shows grafted 'VX211'.

Plant: The growth habit of the tree is illustrated in FIG. 6. This 10 year old tree is approximately 7.3 meters in height with a canopy diameter of approximately 5 meters. The trunk circumference at 1.2 meters above ground level is about 0.61 meters. The bark and year-old branches are light brown (2.5Y 7/2) (FIG. 7). New shoots are green (5GY 7/6). Lenticels (approximately 12 per 2.5 square cm) are slightly lighter than the bark (2.5Y 8/2). The 3 year old trees are 4.3–4.9 meters tall (FIG. 8). The bark is brownish-green (2.5GY 5/8) with scattered (22/2.5 square cm.) buff-colored lenticels (7.5YR 8/2) (FIGS. 9, 10). The six month old greenhouse grown tree is about 35 cm. tall and the main stem is about 1 cm. in diameter (FIG. 11) and green (5GY/10). Lenticels about 0.5 mm long are more dense at the base of the plant and are a buff color (2.5Y 8/4). Graft take is in the normal range for seedling 'Paradox' walnuts (FIG. 12).

Figure 13:
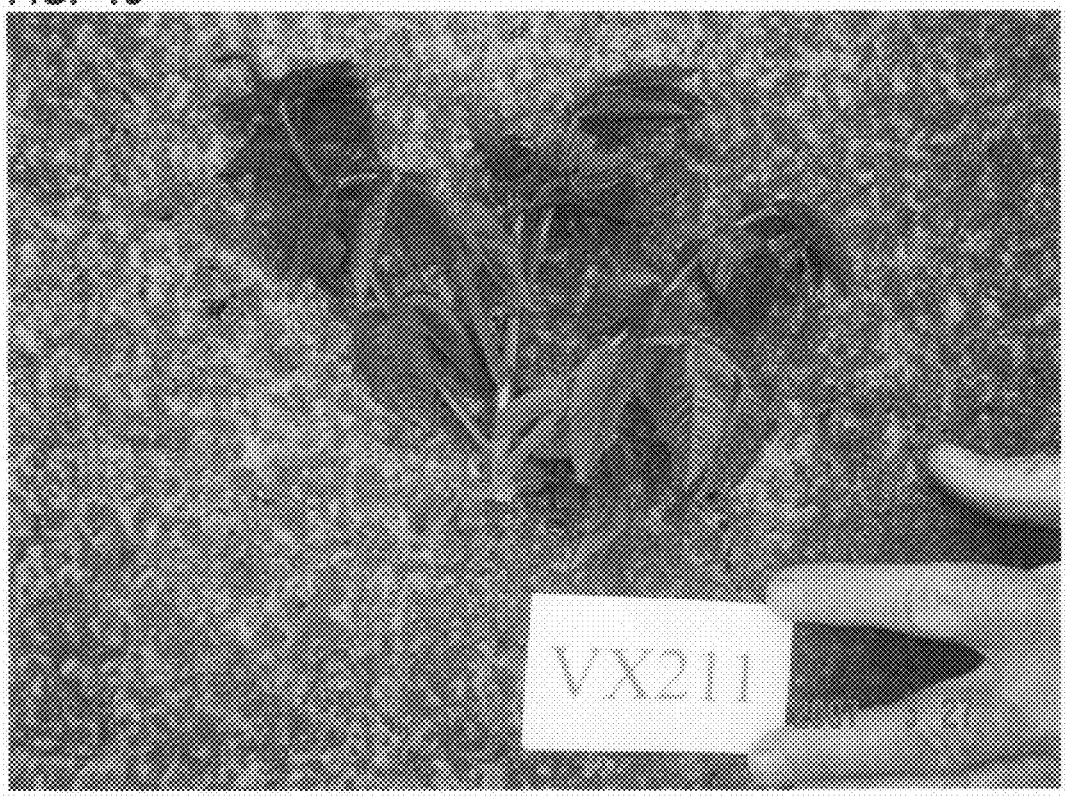
FIG. 13 shows spring foliage of 'VX211'.
Figure 14:
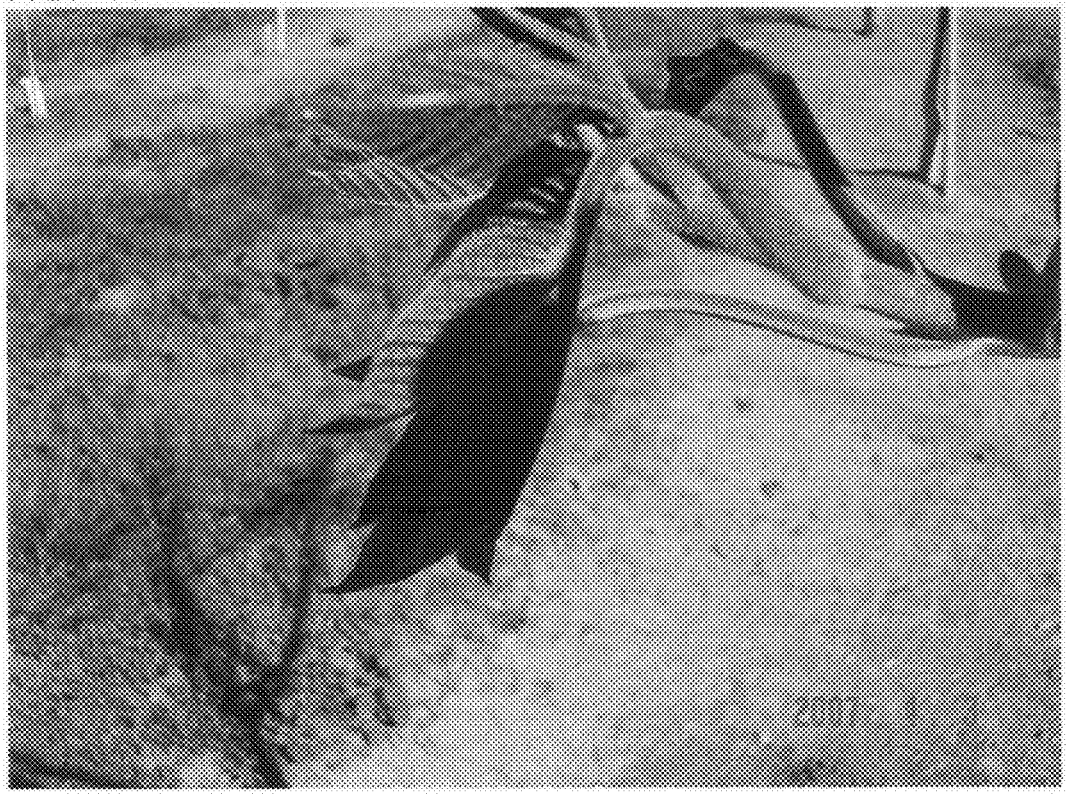
FIG. 14 shows deep red of new foliage of 'VX211'.
Figure 15:
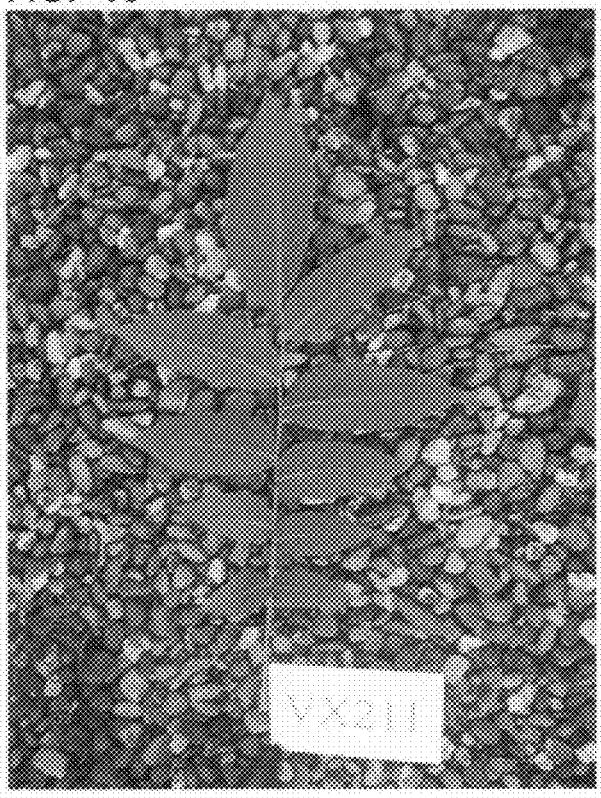
FIG. 15 shows upper side of mature leaf of 'VX211'.
Figure 16:
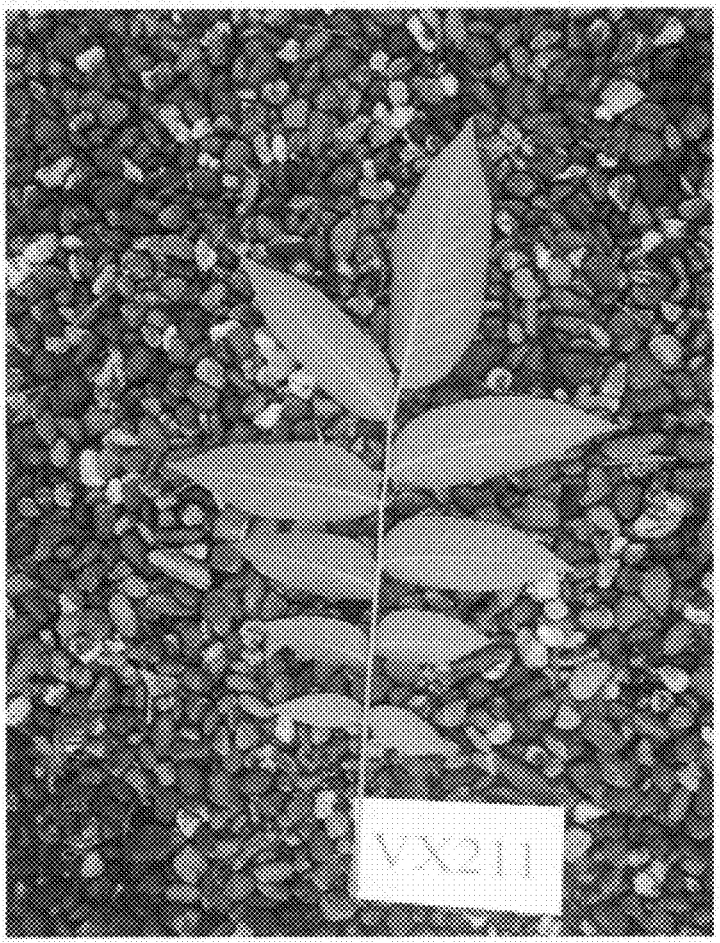
FIG. 16 shows lower side of mature leaf of 'VX211'.

Foliage: The slightly pubescent new spring foliage has a reddish hue to it (10R 4/8), darkest towards the tip (FIGS. 13 and 14) turning green (5GY 5/6) as the leaves get older. The leaves are smooth and the margins are entire (not serrate). The leaves are pinnately compound with 13–15 leaflets. The mature leaves of the 6 month old plant have 9–11 leaflets and are 30 cm long and 23 cm wide. The number of leaflets may vary depending on the age and size of the plant. The upper leaf surface is bright green and the same color as the stem (5GY 5/10) (FIG. 14). The lower surface is slightly duller (5GY 6/6) (FIG. 16). The leaflets are about 5 cm wide and 14 cm long with a petiole 4–8 cm long.

Inflorescence: No catkins or female flowers appeared in the first 10 years. The tree is probably male sterile as is typical with *Juglans hindsii*×*Juglans regia* hybrids. No nuts were observed.

Disease resistance and susceptibility: This rootstock is typical of other *Juglans hindsii*×*Juglans regia* hybrids except that it possesses higher vigor and ability to survive heavy nematode loads. It is also less susceptible to *Phytophthora citricola* than other similar hybrids.

Usage: The new rootstock of the present invention provides walnut growers with a new clonally propagated 'Paradox' rootstock. It can be easily micropropagated.

TABLE 1

Clones grown in Stanislaus County, California in 2004

| Clone | Planted N | Graft-able N | Graft-able % | Diameter (mm) Mean | SD | Range | CV |
|---|---|---|---|---|---|---|---|
| Nematodes | | | | | | | |
| VX211 | 106 | 87 | 82 | 31 | 4.9 | 21-44 | 12.6 |
| *Phytophthora* | | | | | | | |
| AZ2 | 230 | 151 | 66 | 26 | 5 | 13-38 | 19.2 |
| AZ3 | 49 | 24 | 49 | 25 | 6.7 | 11-37 | 26.8 |
| NZ1 | 172 | 111 | 64 | 26 | 4.4 | 10-39 | 16.9 |
| JX2 | 246 | 191 | 78 | 29 | 4.1 | 13-39 | 14.1 |
| RX1 | 104 | 78 | 75 | 18 | 1.6 | 14-22 | 8.8 |
| AX1 | 163 | 86 | 53 | 27 | 4.3 | 14-40 | 15.9 |
| GZ1 | 108 | 83 | 77 | 26 | 5.4 | 13-40 | 20.8 |
| Px1 | 247 | 154 | 62 | 26 | 4.6 | 12-40 | 17.7 |
| AZ1 | 52 | 38 | 73 | 30 | 4.4 | 22-43 | 14.7 |
| UX1 | 27 | 23 | 85 | 25 | 4 | 15-30 | 16 |
| GZ2 | 47 | 38 | 81 | 26 | 4.5 | 15-33 | 17.3 |
| Blackline | | | | | | | |
| WIP3 | 158 | 66 | 42 | 26 | 5 | 12-35 | 19.2 |
| WIP2 | 10 | 6 | 60 | 25 | 2.3 | 23-99 | 9.2 |
| Control | | | | | | | |
| UX022 | 71 | 59 | 83 | 23 | 3.7 | 14-29 | 16.1 |
| English | | | | | | | |
| Vina | 14 | 10 | 71 | 18 | 3.7 | 13-24 | 20.5 |
| Sunland | 64 | 20 | 31 | 26 | 3.8 | 18-31 | 14.6 |
| Totals | 1868 | 1225 | 66 | 25 | | | |

TABLE 2

Walnut Rootstock Orchard Trials-Yuba County.
Established May 2005. Randomized complete block design with 4 clonal and 1 seedling 'Paradox' rootstock.
Twelve single tree replicates.
All rootstocks generally grew well except AZ2. Midday stem water potential measurements suggest that replants and adjacent orchard trees were generally in a similar range to the replants. AZ2 did not grow well despite having midday stem water potentials in a similar range to adjacent trees and the other replants. There was 100% survival of all replant sources.

| Treatment | June 2005 Growth Rating* | June 2005 Diameter (mm) | December 2005 Diameter (mm) | November 2006 Diameter (mm) | % Change (June 2005 to November 2006) |
|---|---|---|---|---|---|
| VX211 | 3.0 | 29.0 | 31.2 | 42.5 a | +46.6 |
| AZ2 | 2.0 | 26.9 | 28.5 | 26.2 c | −2.6 |
| NZ1 | 2.9 | 23.5 | 25.8 | 35.6 b | +51.4 |
| JX2 | 2.2 | 23.7 | 26.4 | 35.2 b | +48.5 |
| CONTROL | 1.4 | 20.5 | 22.4 | 30.0 bc | +46.3 |

*rootstocks were headed near or below 2005 diameter measurement point.
2006 measurement is on new shoot growing above previous cut.
*Growth rating descriptions:
0 No growth
1 Just breaking
2 Moderate growth
3 Vigorous growth

TABLE 3

Field performance of clonal 'Paradox' walnut hybrids, Northern California black walnut and Chinese wingnut rootstocks in non-infested soil and soil infested with *Phytophthora*.

| Clone (or species) | Maternal background of hybrid (or species of standard) | Soil treatment (January 2006) | Incidence of crown rot (%) |
|---|---|---|---|
| AX1 | *californica* | Control | 0 c |
| | | *P. citricola* | 4 c |
| AZ2 | (major x *hindsii*)x *nigra* | Control | 0 c |
| | | *P. citricola* | 0 c |
| NZ1 | (major x hindsii)x *nigra* | Control | 0 c |
| | | *P. citricola* | 0 c |
| GZ1 | *hindsii* | Control | 0 c |
| | | *P. citricola* | 4 c |
| JX2 | *hindsii* | Control | 0 c |
| | | *P. citricola* | 0 c |
| PX1 | *hindsii* | Control | 0 c |
| | | *P. citricola* | 8 bc |
| VX211 | *hindsii* | Control | 0 c |
| | | *P. citricola* | 0 c |
| RX1 | *microcarpa* | Control | 0 c |
| | | *P. citricola* | 0 c |
| WIP3 | *hindsii* x *regia* | Control | 0 c |
| | | *P. citricola* | 8 bc |
| (NCB) | (*J. hindsii*) | Control | 16 b |
| | | *P. citricola* | 62 a |
| (Wing-nut) | (*Pt. stenopiera*) | Control | 0 c |
| | | *P. citricola* | 0 c |

| Clone (or species) | Percent of trunk circ. Necrotic | Incidence of tree mortality (%) | Increase in trunk circ. (mm) |
|---|---|---|---|
| AX1 | 0 c | 0 c | 163 c |
| | 1 c | 0 c | 146 cde |
| AZ2 | 0 c | 0 c | 116 fg |
| | 0 c | 0 c | 117 fg |
| NZ1 | 0 c | 0 c | 116 fg |
| | 0 c | 0 c | 130 def |
| GZ1 | 0 c | 0 c | 157 cd |
| | 1 c | 0 c | 150 cd |
| JX2 | 0 c | 0 c | 166 bc |
| | 0 c | 0 c | 135 def |
| PX1 | 0 c | 0 c | 169 bc |
| | 1 c | 0 c | 157 cd |
| VX211 | 0 c | 0 c | 191 b |
| | 0 c | 0 c | 147 cde |
| RX1 | 0 c | 0 c | 112 fg |
| | 0 c | 0 c | 116 fg |
| WIP3 | 0 c | 0 c | 100 g |
| | 2 c | 0 c | 121 efg |
| (NCB) | 17 b | 17 b | 65 h |
| | 59 a | 59 a | 57 h |
| (Wingnut) | 0 b | 0 c | 226 a |
| | 0 b | 0 c | 193 b |

[1]All trees were planted May 2005. The assessments of crown rot and mortality were made 21 Nov. 2006. Means within a column and without letters in common are significantly different (Waller k ratio).

What we claim is:

1. A new and distinct variety of walnut rootstock plant designated 'VX211' as shown and described herein.

* * * * *